United States Patent [19]

Laurain

[11] Patent Number: 5,108,395
[45] Date of Patent: Apr. 28, 1992

[54] IMPLANT FOR ANTERIOR DORSOLUMBAR SPINAL OSTEOSYNTHESIS, INTENDED FOR THE CORRECTION OF KYPHOSES

[75] Inventor: Jean-Marie Laurain, Besancon, France

[73] Assignee: Societe de Fabrication de Materiel Orthopedique - Sofamor, Paris, France

[21] Appl. No.: 584,571

[22] Filed: Sep. 18, 1990

[30] Foreign Application Priority Data

Sep. 18, 1989 [FR] France .............. 89 12187

[51] Int. Cl.$^5$ ............................................. A61B 17/56
[52] U.S. Cl. ..................................... 606/61; 606/71; 606/73
[58] Field of Search ............. 606/57, 58, 59, 61, 606/69, 70, 71, 105, 73; 623/16, 17; 128/69; 403/97

[56] References Cited

U.S. PATENT DOCUMENTS

| | | | |
|---|---|---|---|
| 3,242,922 | 3/1966 | Thomas | 606/61 |
| 4,382,438 | 5/1983 | Jacobs | 29/164 |
| 4,411,259 | 10/1983 | Drummond | 128/69 |
| 4,554,914 | 11/1985 | Kapp | 606/61 |
| 4,582,445 | 4/1986 | Warshawsky | 403/97 |
| 4,655,199 | 4/1987 | Steffe | 606/61 |
| 4,657,550 | 4/1987 | Daher | 606/61 |
| 4,805,602 | 2/1989 | Puno | 606/61 |
| 4,827,918 | 5/1989 | Olerud | 606/61 |
| 4,913,134 | 4/1990 | Luque | 606/61 |
| 4,944,743 | 7/1990 | Gotzen | 606/61 |

FOREIGN PATENT DOCUMENTS 0301489 2/1989 European Pat. Off. .
8711992.7 9/1987 Fed. Rep. of Germany .

Primary Examiner—Robert A. Hafer
Assistant Examiner—Michael Brown
Attorney, Agent, or Firm—Wenderoth, Lind & Ponack

[57] ABSTRACT

This implant has in combination a pair of clamps (2) provided with spikes (3) and with screws (5) for fixing to two corresponding vertebrae (V2, V4) and notches (23) to support the tips of the blades of a pair of distraction forceps, a rigid plate (6) for interconnecting the two clamps (2) and whose ends are pierced with orifices (17) in which may engage threaded pieces (12) of the camps (2) and whose length (L) corresponds to the distance between the posterior orifices (9) of the clamps (2) after distraction of the vertebrae, and lastly nuts (7) for rigidly connecting together the plate (6) and the clamps (2). This implant has, in particular, the advantage of permitting distraction by the forceps bearing against the clamps instead of against the vertebrae, which was not possible with the previously known plates; in addition, it is compact while at the same time being sufficiently solid, and thus prevents any risk of rubbing against the aorta.

12 Claims, 4 Drawing Sheets

IMPLANT FOR ANTERIOR DORSOLUMBAR SPINAL OSTEOSYNTHESIS, INTENDED FOR THE CORRECTION OF KYPHOSES

The subject of the present invention is an implant for anterior dorsolumbar spinal osteosynthesis, intended essentially for the correction of kyphoses caused by the destruction of one or two vertebral bodies.

As is known, a kyphosis is a prolapse of the vertebral column towards the front caused by the destruction of a vertebral body which may itself be the result of a trauma (fracture, accident) or of a vertebral tumour. The kyphosis may have a large radius of curvature and be uniform, or conversely be very short (angular kyphosis). These short kyphoses may be caused by benign or especially malignant tumours (metastases) or by recent traumas (comminuted fractures of the vertebral body) or old traumas, but also by congenital deformities (hemivertebra) and by infections (Pott's disease).

Anterior approach to the dorsolumbar spine (and not posterior) is justified for treating such kyphoses, and even in the absence of kyphosis, in the case of tumours affecting the vertebral body.

In order to treat a kyphosis, partial or total ablation of the vertebral body and of the two adjacent vertebral discs is carried out and then, using an appropriate pair of forceps, "distraction" is carried out, in other words extension or stretching of the vertebrae situated on either side of the vertebral body removed. Then either a polymerizable paste or a bone graft which is modelled in order to give it the shape of the body destroyed is introduced into the space left free. Next an osteosynthesis instrument is positioned which is adapted to connect the two vertebrae, the upper and the lower, to the interposed graft or paste so as to prevent any relative movement between them.

Thus any affection of the vertebral body requiring an anterior approach entails what may be termed the anterior reconstruction of the dorsolumbar spine (dorsal and lumbar spine) even though it is known that problems often arise for the dorsolumbar hinge.

Anterior reconstruction of the dorsolumbar spine is thus based on two elements: replacement of the vertebral body and osteosynthesis. The replacement of the vertebral body is carried out using an autogenous bone graft (autograft) or an allogenic bone graft (allograft), using bone substitutes (PMMA—polymethyl methacrylate—cement, acrylic prosthesis, coral, lyophilized animal bone, etc.).

The osteosynthesis is to stabilize the fitting. When a bone graft is used, it must be sufficiently solid to ensure stability until the graft has been incorporated into the adjacent vertebral bodies (approximately six months). The consolidated bone graft will then ensure the permanent stability of the spinal segment, the osteosynthesis equipment normally not being subjected to any further mechanical stresses. If an inert substance is used as a substitute for the vertebral body, the substitute and the osteosynthesis must together ensure the stability of the spinal segment for as long as possible. In both cases, the osteosynthesis equipment must be as solid as possible.

There are essentially two categories of devices known for carrying out this anterior reconstruction of the dorsolumbar spine: devices permitting distraction and devices not permitting such distraction.

In the first category, several types of distraction systems exist but they have the same principle: one or two screws are fixed to the vertebral body of the vertebrae adjacent to the vertebra with the lesion. They are connected by one or two rods enabling distraction to be effected (and thus the kyphosis to be corrected). The rods are then fixed to the screws, which enables the fit between the two vertebral bodies to be stabilized. These systems have the advantage of permitting distraction but are not sufficiently stable if they have one rod, or are too bulky and cumbersome if they have two rods. This excessive size may cause certain elements of the system to rub against the neighbouring aortic artery, which rubbing may in turn give rise to serious complications (false aneurysms). Moreover, this is the reason why the use of some of these distraction systems is now prohibited.

The second category of devices essentially consists of plates whose shape attempts to match the morphology of the spine. These plates are fixed by two or three screws at their ends, and where necessary in their middle part, to the vertebral bodies. They are less thick, and hence less bulky, than the previous systems whilst at the same time usually being more solid. On the other hand, since they are purely static, they do not enable direct distraction to be performed, and hence an instrumental correction of the kyphosis. Lastly, when using these plates, the positioning of the bone graft is awkward for a surgeon because of the inconvenience caused by the presence of the clamp for spacing apart the two vertebral bodies.

The object of the invention is therefore to provide an implant having the advantages of these two categories of prior devices without having their disadvantages so as to carry out an anterior reconstruction of the dorsolumbar spine in one or two regions with a lesion, enabling the kyphosis to be corrected.

According to the invention, the implant is characterized in that it comprises in combination:

a) a pair of clamps provided with means for fixing to two corresponding vertebrae situated on either side of a damaged vertebra, as well as means for supporting the ends of the blades of a pair of forceps for distracting the two abovementioned vertebrae, b) a rigid plate for interconnecting the two clamps and whose length corresponds to the distance between the clamps after distraction of the vertebrae carrying the said clamps, c) means for rigidly connecting together the plate and the clamps.

The provision on the clamps of means for supporting the ends of the blades of a pair of forceps enables the distraction of the spinal segment to be carried out without inconveniencing the positioning of the bone graft or of the cement in the space freed by the ablation of the intermediate vertebral body. Indeed, the ends of the forceps are supported on surfaces of the implant itself, and therefore completely outside the space reserved for the graft. This represents an essential advantage of the invention as compared with the prior plates.

According to a feature of the invention, each clamp has on its face intended to be applied against the associated vertebral body a convexity extending from top to bottom and complementing the concavity of the vertebral body, and a concavity extending from front to rear and adapted in order to fit tightly against the anteroposterior convex lateral face of the said vertebral body.

The combination of this convexity in the vertical direction and this concavity in the lateral direction advantageously permits excellent anatomical adaptability of the implant.

According to another feature of the invention, the implant comprises means for adjusting the angle of the plate relative to the clamps and for locking the plate in rotation on the clamps in an anatomical sagittal plane; these means may be mating radiating serrations arranged on the opposite faces of the end parts of the plate and of the clamps, around holes for the passage of a screw through the plate and the clamp.

The adjustment of the angle of the plate and its locking in rotation relative to the clamps therefore take place with an accuracy corresponding to the pitch of the serrations, it being possible to adapt the latter to the difference in the parallelism of the anteroposterior axes of the vertebral bodies.

According to an embodiment of the invention, each clamp has a central tubular part coaxial with a through hole for a screw, which part is adapted in order to be traversed by this screw and in order to engage in a corresponding through orifice in the end of the plate, and this tubular part is arranged so as to interact with a means for connecting the plate to the clamp.

The said connecting means may be a nut capable of being screwed onto a external thread of the tubular part of the clamp, and on which is arranged a peripheral annular shoulder for bearing against the corresponding end part of the plate, thus held tightly between the clamp and the nut, with the result that the screwing in of this nut renders the assembly formed by the plate and the clamp integral.

The means for supporting the tips of the blades of a pair of forceps for distracting the vertebrae are, for example, notches formed on the clamps.

The implant according to the invention may thus be fitted by distraction whilst at the same time being compact as compared with prior known distraction systems (absence of threaded rods and transverse connecting plates).

Other features and advantages of the invention will emerge in the course of the following description made with reference to the attached drawings which illustrate one of its embodiments by way of non-limiting example.

FIG. 4 is a diagrammatic cross-sectional view of a patient in the horizontal plane in the dorsolumbar region, showing the initial phase of the surgical operation.

FIG. 5 is a diagrammatic view in elevation of the spinal segment before undergoing the operation.

FIG. 6 is a diagrammatic view in elevation of the spinal segment after the clamps of the implant have been fitted.

FIG. 7 is a diagrammatic view in elevation of the spinal segment during the distraction of the vertebrae by way of an ancillary pair of forceps.

FIG. 8 is a view similar to FIG. 7 showing the positioning of the graft between the vertebrae carrying the clamps.

FIG. 9 is a view in elevation of the distracted spinal segment on which the implant according to FIGS. 1 to 3B is fixed.

Figure 1:
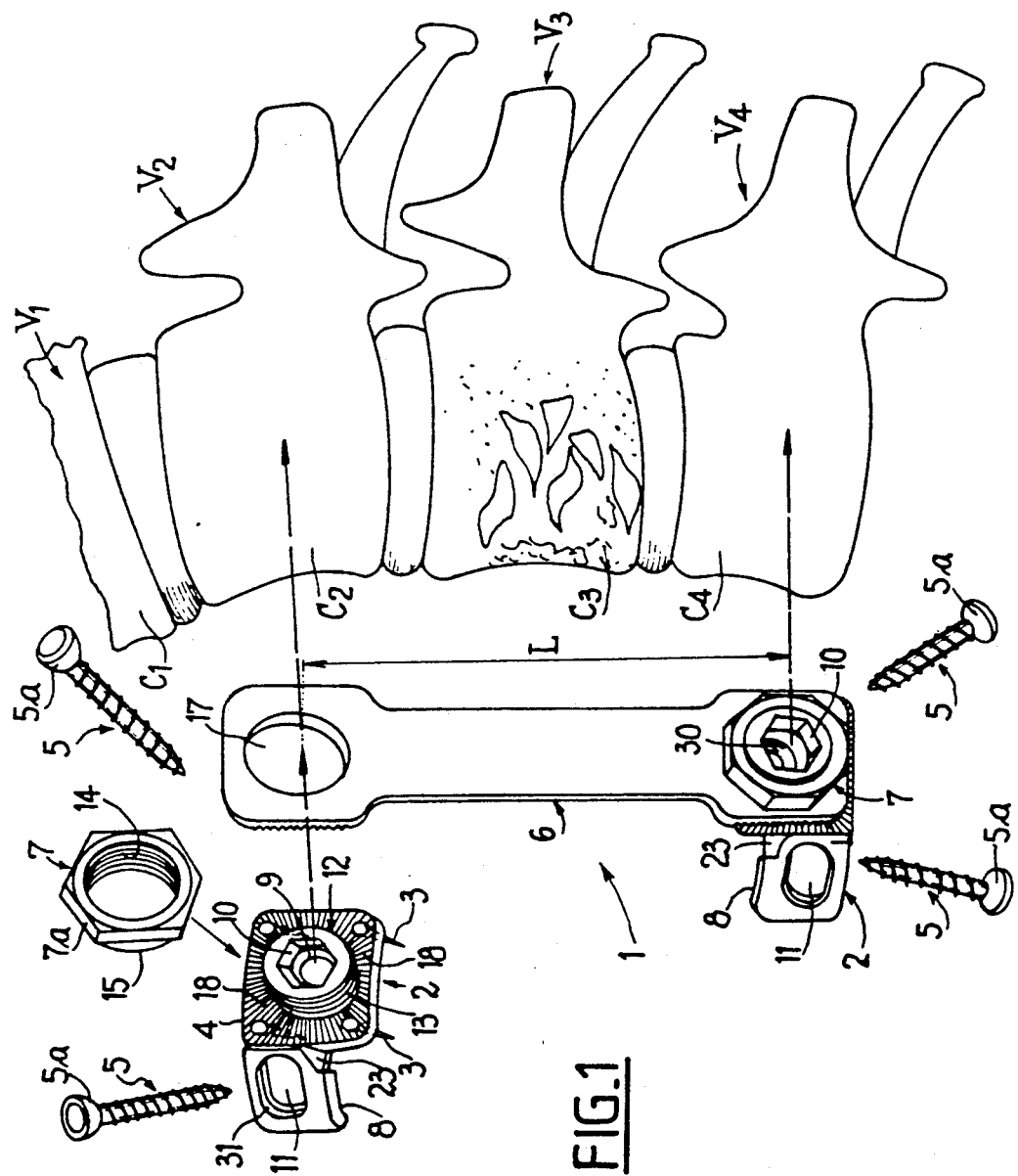
FIG. 1 is an exploded perspective view of an embodiment of the dorsolumbar spinal osteosynthesis implant according to the invention, as well as of the corresponding spinal segment affected by a kyphosis.

In FIG. 1 a spinal segment can be seen with four dorsolumbar vertebrae V1, V2, V3, V4 having vertebral bodies C1, C2, C3, C4, one C3 of which has been virtually destroyed by a trauma or by a tumour, which creates a kyphosis which it is the object of the osteosynthesis implant 1 to treat.

The implant 1 intended to be fitted anteriorly onto the vertebral bodies C2 and C4 flanking the destroyed body C3 comprises the following elments:

a pair of clamps 2 provided with means for fixing to the two corresponding vertebral bodies C2, C4, which means consist in the example shown of four spikes or studs 3 integral with the body 4 of each clamp 2, and of two vertebral screws 5 traversing each clamp 2;

a rigid plate 6 interconnecting the two clamps 2 and whose length L corresponds to the distance between the clamps 2 after distraction of the vertebrae V2, V4 carrying the clamps 2;

nuts 7 for rigidly connecting the plate 6 to the clamps 2.

The body 4 of each clamp 2 is extended by a lateral lug 8, preferably integral with the body 4. The body 4 and the lug 8 are pierced by two respective spherical holes 9, 11 for receiving two complementary spherical heads 5a of the screws 5. This enables the body to be oriented in the desired direction inside the vertebral bodies C2 and C4 in which they are to be inserted, and to the width of which the length of the screws 5 is moreover adapted. Furthermore, the hole 11 of the lug 8 has an oblong shape in its anterior part so as to offer the possibility of additional adjustment, and terminates at its posterior part in a spherical seat 31 for the spherical head 5a of a screw.

A tubular part 12 having an external thread 13 adapted in order to interact with a complementary internal thread 14 of the associated nut 7 extends, coaxially with the central hole 9 of each clamp, in the anterior direction, and hence in the direction opposite the corresponding vertebral body C2 or C4. The tubular piece 12 has at its posterior end a thread 20 of diameter less than that of its anterior part and which enables the piece 12 to be screwed into the tapped hole 9. The posterior end of the inner wall of the piece 12 forms a spherical seat 30 adapted so as to receive a head 5a of a screw 5, while a hexagonal profile 10 is provided in its anterior end in order to enable it to be screwed into the body 4 by an appropriate tool.

Figure 3A:
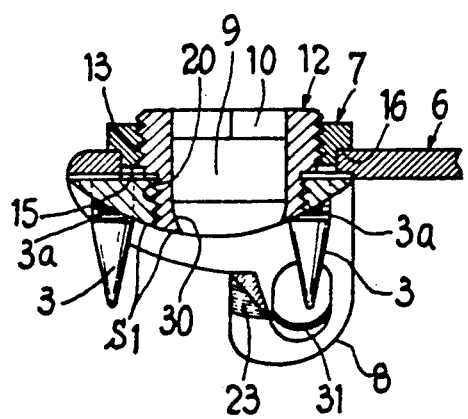
FIG. 3A is a view in cross-section along AA in FIG. 3B of the clamp.
Figure 3B:
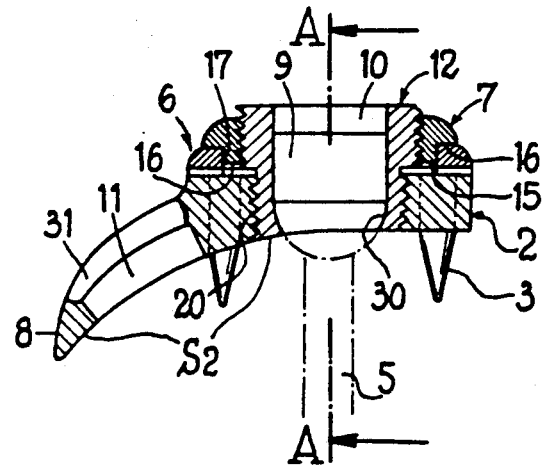
FIG. 3B is a view in cross-section along BB in FIG. 2 of the clamp.

Each end part of the plate 6 is pierced with an orifice 17 whose diameter is greater than the external diameter of the threaded part 12 such that the latter may engage in the orifice 17. Each nut 7 has an appropriate polygonal outer profile 7a, for example hexagonal, in order to receive a corresponding screwing tool. An annular shoulder 16, adapted so as to bear against the periphery of an orifice 17 of the plate 6, is arranged between this profile 7a and a posterior collar 15 (FIGS. 3A and 3B). The projecting end of the collar 15 is simultaneously placed between the threaded part 12 and the edge of the hole 17 when the screwing of the nut 7 onto the threaded part 12 is complete. The screwing of each nut 7 onto the tubular parts 12 thus causes the assembly consisting of the plate 6 and the two clamps 2 to be made integral.

Each clamp 2 has on its anterior face intended to be applied to the associated vertebral body C2 or C4 a convexity S1 (FIG. 3A) extends from top to bottom and complementing the concavity of the vertebral body, and a concavity S2 (FIG. 3B) extending from front to rear adapted in order to fit tightly against the anteroposterior convex lateral face of the vertebral body C2 or C4. The surfaces S1 and S2 are defined by the body 4, the end of the piece 12 and the lug 8.

Figure 9:
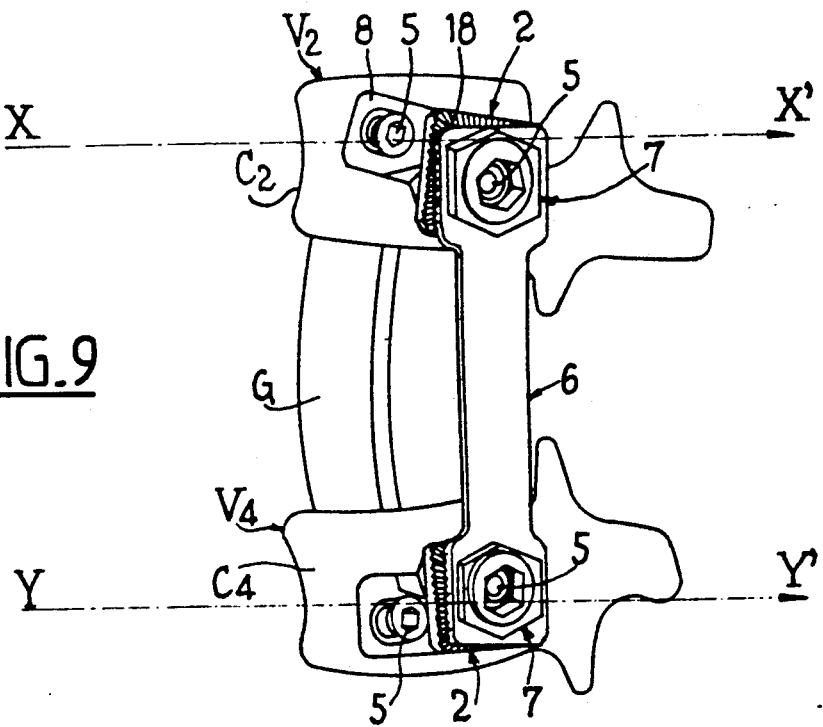

The implant 1 moreover has means for adjusting the angle of the plate 6 relative to the clamps 2 and for locking in rotation the plate 6 on the clamps in a sagittal plane. In the embodiment shown, these means are radiating serrations 18 provided on the outer face of each body 4 around the posterior orifice 9 and around the threaded part 12, and mating radiating, or radial, serrations 19 cut in the inner face of the end parts of the plate 6 around orifices 17. The serrations 18, 19 have an appropriate angular pitch, for example 4°, and enable the plate 6 to be oriented freely in the sagittal plane relative to the clamps 2, in other words virtually in the plane of the plate 6. This angular adjustment enables the plate 6 to be adapted to any difference in the parallelism between the anteroposterior axes XX' and YY' of the vertebrae V2 and V4 (FIG. 9).

Figure 7:
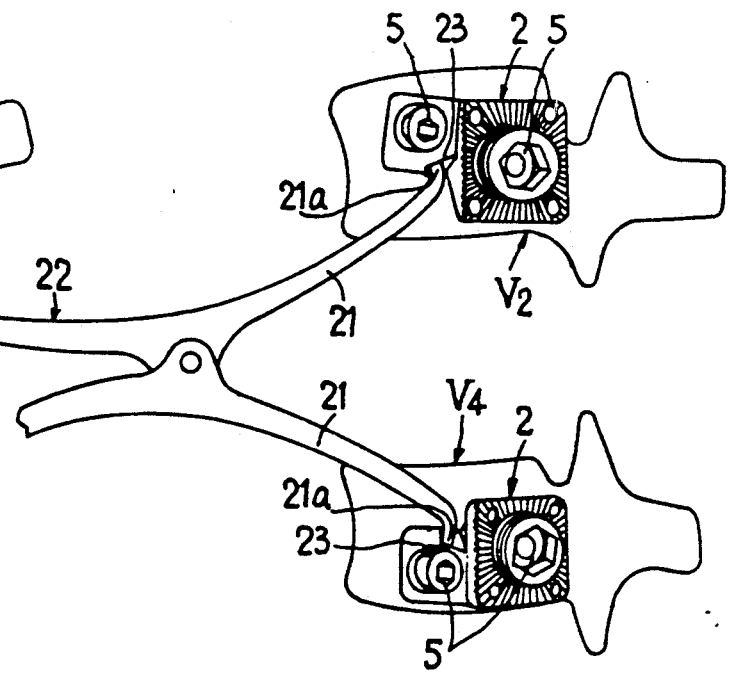

The implant 1 is also provided with means for supporting the tips 21a of the blades 21 of a pair of forceps 22 (FIGS. 7 and 8) for distracting the vertebrae V2 and V4. In the example shown, these means consist of notches 23 formed on the clamps 2, one notch 23 per clamp, for example on its lateral lug 8 in the vicinity of the join between the lug 8 and the body 4.

Figure 2:
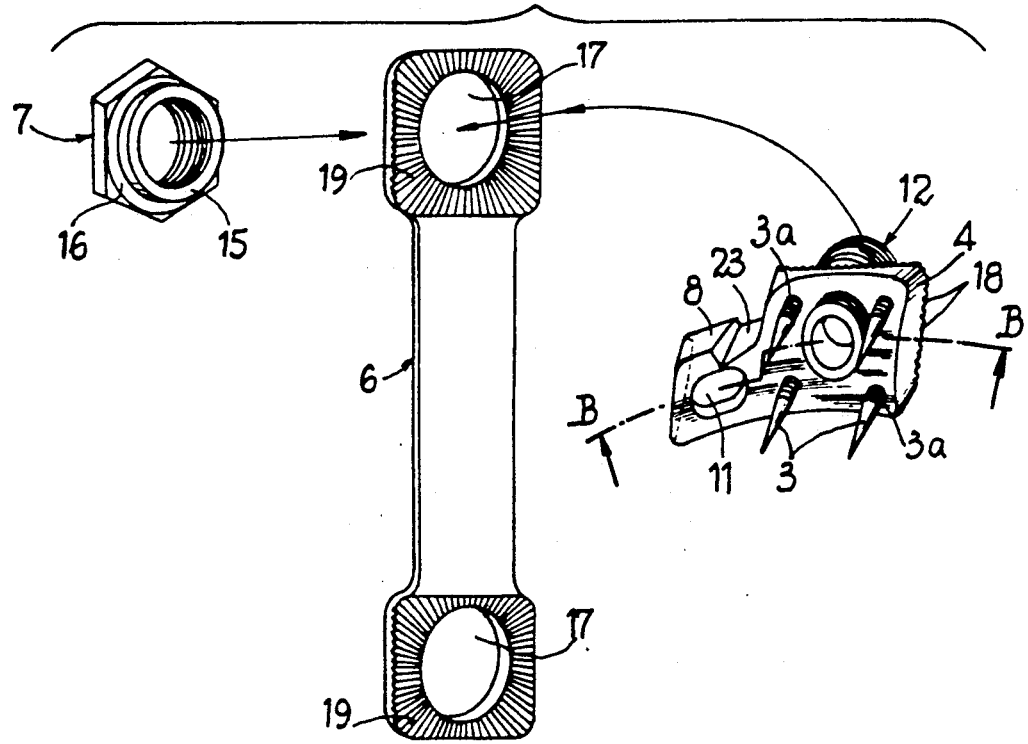
FIG. 2 is a plan view from underneath of the plate, of a clamp and of a nut of the implant in FIG. 1.

The spikes 3 are fixed at four corners of the posterior part of each clamp 2, to the inner face, so as to stabilize the clamps in the vertebral bodies C2, C4 immediately opposite one another before fitting the screws 5. Each spike 3 is provided over a part of its length with an anti-return toothing 3a (FIGS. 2 and 3a).

The holes 9, 11 are offset in terms of height (FIG. 3B) so as to prevent contact between the convergent screws 5. The clamps 2 are shorter in their anterior part (for example 12 mm), which gives them an asymmetric configuration.

By way of non-limiting numerical example, each clamp 2 may measure 30 mm from front to rear, 20 mm high and 4 mm thick.

The screws 5 are standard screws for spongy bone, with a long thread, with a diameter of for example 6.5 mm, and have an internal hexagonal recess on their spherical head 5a in order to enable them to be screwed in by an appropriate tool. Their length varies as a function of the width of the vertebral body and must be able to include the two cortices. The spherical shape of the seats 30 for the spherical heads 5a in the clamps 2 enables the path of the screws 5 to be directed in the desired direction. Thus the clearance is approximately 15° for the posterior orifice 9 and even more in the horizontal plane for the anterior orifice 11 by virtue of its oval shape. Each clamp 2 is fixed to the vertebral body by two screws 5.

The plate 6 may be adapted in terms of height to the distance between the two clamps 2. This distance is dependent on the correction of the kyphosis performed using the distracting forceps 22 which bear on the clamps 2. It is particularly important that the length L of the plate 6 be equal to the distance between the two orifices 17 measured from the centers of the orifices, so as to be adapted perfectly to the distance between the two clamps 2, and not vice versa. This requires a set of plates 6 of lengths increasing, for example, in 2 mm increments. A set of 12 plates from 50 to 72 mm may thus be used.

By way of a guiding numerical example, the plate 6 may measure 2 mm thick, 13 mm wide at its center, and wider at its end parts (20 mm) which are pierced with orifices 17, for example 15 mm in diameter, corresponding to the external diameter of the threaded tubular part 12 over which these end parts are fitted.

Nuts 7, 17 mm and 4.5 mm thick for example, complete the plate 6/clamps 2 assembly.

The ancillary equipment comprises seven types of instruments known per se with the exception of the distracting forceps 22, it alone being shown (FIGS. 7 and 8):

1) The distal blades 21 are bent back at their bifid tips 21a adapted in order to fasten in the corresponding notches 23 of the clamps 2. The clearance between the blades 21 may be from 35 to 80 mm approximately.

2) Hexagon, straight and cardan screwdriver, spanner, for example 17 mm, large size and small size for working at depth, clamp-holder enabling the clamp 2 to be anchored before fitting the screws 5, nut-holder, for example 17 mm, enabling the nut 7 to be positioned on the threaded piece 12, plate-holder, plate-measuring instrument enabling the distance between the centre of the posterior orifices 9 of the clamps 2, and hence the exact length L of the plate 6, to be measured.

The implant 1 described hereinabove applies to the lumbar spine and to the dorsolumbar hinge as far as and including the tenth dorsal vertebra. It is possible to produce smaller clamps 2 using the same plates for the remainder of the dorsal spine.

The operating technique for fitting the implant 1 which has just been described is as follows.

Figure 4:
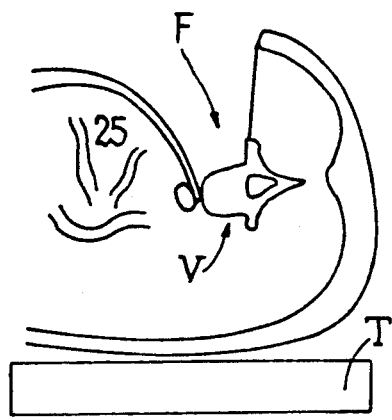
FIGS. 4 to 9 are views illustrating the operating sequence for fitting the implant in FIGS. 1 to 3B onto a dorsolumbar spinal segment affected by a kyphosis.

The surgeon approaches the spinal segment of the patient suffering from kyphosis, lying on his side on the operating table T, anterolaterally (FIG. 4) in the direction of the arrow F towards the column V, moving to one side the viscera 25: lobotomy for the lumbar spine, transpleural subperitoneal thoracophrenic laparotomy for the dorsolumbar hinge, preferably on the left side; transpleural thoracotomy for the dorsal spine, preferably on the right side.

Figure 5:
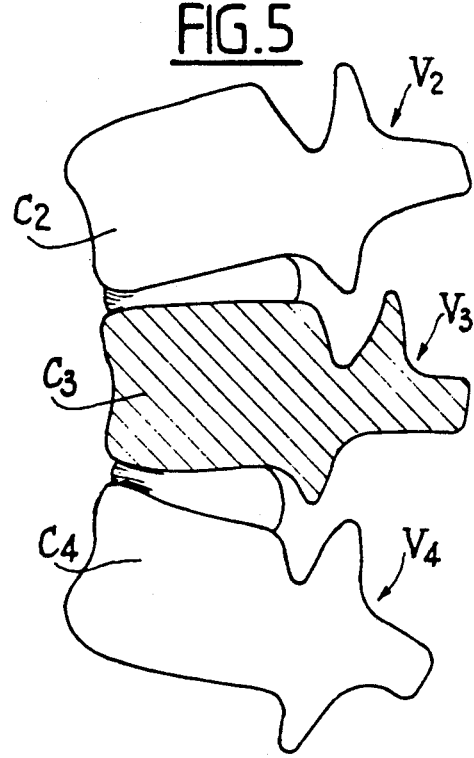

The surgeon then performs a discectomy and a corporectomy on the vertebra V3 with a lesion in order to remove its vertebral body C3 (FIG. 5) and the adjacent vertebral discs.

Figure 6:
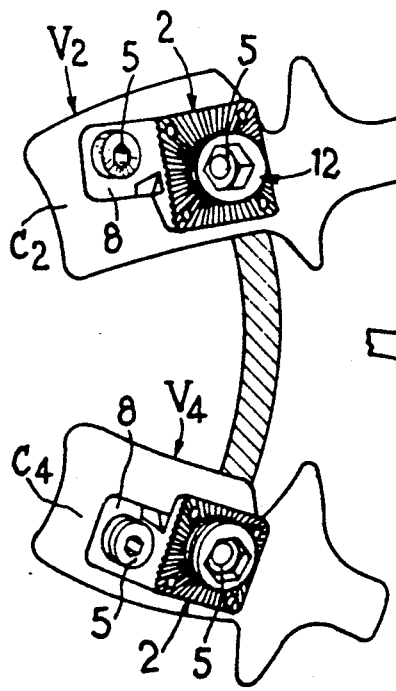

The two clamps 2 are then placed (FIG. 6) on the adjacent vertebral bodies C2, C4 by pushing spikes 3 into them, orienting the clamps 2 such that their convexity S1 and their lateral concavity S2 match well the corresponding concavity and convexity of the vertebral bodies, and such that the notches 23 of each clamp 2 are positioned towards the vertebra with a lesion V3. Each clamp 2 is then fixed by two screws 5 for which the appropriate length will have been calculated beforehand, these screws thus traversing the holes 9 and 11 and their heads 5a being applied against the complementary spherical seats 30, 31.

The surgeon then fits the distracting forceps (FIG. 7), the tips 21a of which fit into the notches 23 against which they bear, so as to permit distraction and to correct the kyphosis.

Figure 8:
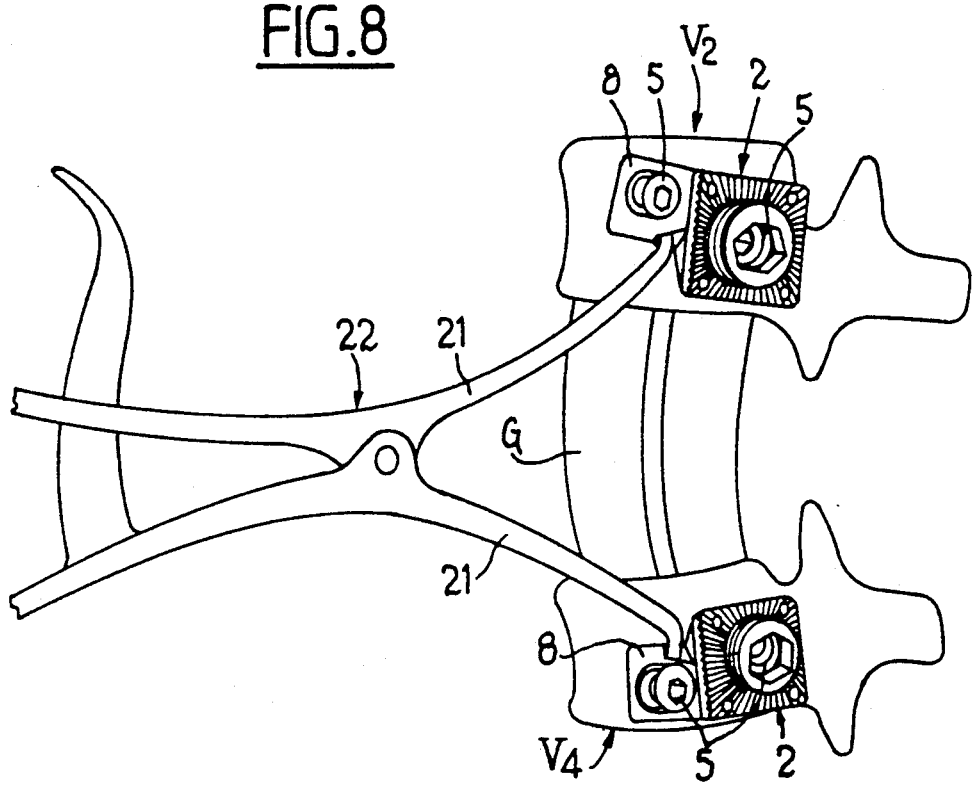

A graft G or bone substitutes are then introduced into the intermediate space freed by the ablation of the vertebral body C3. The distracting forceps 22 are left in place with a slight hypercorrection. By virtue of its configuration, it in no way inconveniences the positioning of the grafts (FIG. 8). The distraction is then released slightly so as to impact the graft G thoroughly.

The distance between the centers of the posterior orifices 9 relative to the vertebra is then measured using the measuring instrument so as to select a plate 6 with a perfectly adapted length L. The selected plate 6 is then fitted at its ends over the threaded parts 12 which traverse the orifices 17. Lastly, a nut 7, whose anterior collar 15 is placed in between the thread 13 and the edge of the orifice 17 (FIGS. 3A and 3B) while its shoulder 16 sandwiches the plate 6 against the serrated surface of the body 4, is fitted onto each threaded part 12. The surgeon adjusts the relative angular position of the plate 6 and the clamps 2, the plate 6 being locked in rotation in the orientation selected by the mutual engagement of the complementary serrations 18 and 19. Lastly, the nuts 7 are force-tightened (FIG. 9).

The technical advantages of the implant according to the invention are as follows.

Firstly and as already indicated, employing clamps 2 which are anchored beforehand on the vertebral bodies adjacent to the vertebral body destroyed, and which are provided with bearing surfaces 23 for the tips 21a of the distracting forceps 22, enables the intervertebral distraction to be performed manually, preventing any direct bearing force on the vertebrae, which considerably facilitates the insertion of the bone grafts (or substitutes) and their locking in place with prestress (impaction).

Furthermore, the rigid assembly obtained after tightening the nuts 7 is sufficiently solid to enable the bone graft to consolidate or to prevent the destabilization of the bone substitute.

The convex S1 and concave S2 surfaces and the sets of plates 6 of different lengths advantageously permit the anatomical adaptability of the clamps to the vertebrae.

By virtue of the presence of the plate 6, the implant 1 according to the invention is both sufficiently solid and compact and there is therefore no risk of dangerous rubbing against the aorta occurring. In use, this implant thus fully provides the desired safety.

Lastly, means for adjusting the angle of the plate 6 relative to the clamps 2 and for locking in rotation (complementary serrations 18 and 19) enable the implant to be fitted with a maximum amount of flexibility, and likewise adaptability to the anatomical conditions of the spinal segment in question.

The embodiment described may have numerous alternative embodiments. Thus the nuts 7 could be replaced by any other equivalent means enabling the plate 6 and the clamps 2 to be connected rigidly, the complementary serrations 18, 19 may likewise be replaced by any other equivalent means. The fixing screws 5 may number more than two, it then being possible for each clamp 2 to be provided with an additional lug or with a lug sufficiently large to receive two fixing screws. The piece 12 could likewise be produced integral with the body 4, the lug 8 and the spikes 3 which may have no anti-return toothing.

I claim:

1. A vertebral implant for the anterior removal and a reconstruction of damaged vertebrae which comprises in combination:

a) a pair of clamps, each provided with a means for fixing said clamp to a vertebra situated on either side of a damaged vertebra and provided with a means for supporting a forcep blade tip for distracting the vertebrae from the damaged vertebra with a pair of forceps, b) a rigid elongate plate for interconnecting said pair of clamps having an opening provided at each opposite end and having a predetermined length between said openings which corresponds to the distance between said pair of clamps after distraction of the vertebrae from the damaged vertebra, and c) means for rigidly connecting together each of said clamps to said rigid elongate plate.

2. A vertebral implant according to claim 1, wherein said means for fixing said clamps to the vertebrae comprises a plurality of spikes and screws.

3. A vertebral implant according to claim 2, wherein said screws comprise first and second screws, and wherein each of said clamps is provided with first and second openings adapted for receiving said first and second screws respectively therethrough, said openings being adapted to enable said screws to be oriented in the vertebra in a desired direction.

4. A vertebral implant according to claim 3, which further comprises a means for adjusting the angle of said rigid elongate plate relative to said clamps and for locking said plate in rotation on said clamps in a sagittal plane.

5. A vertebral implant according to claim 4, wherein said angular-adjustment and locking means are interlocking serrations arranged radially on the posterior face of said clamps around said first openings and on said opposing face of said plate ends.

6. A vertebral implant according to claim 3, wherein each of said clamps has a central tubular part projecting from the posterior face defining said first opening therethrough, said central tubular part being passable through said openings of said plate ends, the outer surface of said central tubular part having a means for engaging with said means for rigidly connecting said plate to said pair of clamps.

7. A vertebral implant according to claim 6, wherein said means for engaging on the outer surface of said central tubular part is an external thread, said connecting means is a nut having an internal thread complementary with said external thread of said central tubular part, and said connecting means having a peripheral annular shoulder for contact against the posterior face of said plate end, so that said plate can be integrally held between said pair of clamps and a pair of said nuts.

8. A vertebral implant according to claim 1, wherein each of said clamps has an anterior face for contacting against the associated vertebra which is provided with a convexity extending in a vertical direction along said face which complements the concavity of the vertebrae and a concavity extending in a horizontal direction along said face so that said clamps fit tightly against the anteroposterior convex lateral face of the vertebrae.

9. A vertebral implant according to claim 1, wherein said means for supporting the forcep blade tip is a notch formed on said clamp.

10. A vertebral implant according to claim 1, wherein each of said clamps comprises a body having anchoring spikes provided on an anterior face for anchoring said clamp to the vertebra, a tubular central part projecting from the posterior face of said body defining a first opening for receiving a screw therethrough for anchoring said clamp to the vertebra, a lateral lug integral with said body defining a second opening for receiving a screw therethrough for further anchoring said clamp to said vertebra, and a notch disposed on said clamp for supporting a forcep blade tip for distracting the vertebrae from the damaged vertebra with a pair of forceps.

11. A vertebral implant for the anterior removal and reconstruction of damaged vertebrae which comprises in combination:
   a) a pair of clamps, each provided with a means for fixing said clamp to a vertebra situated on either side of a damaged vertebra and provided with a means for supporting a forcep blade tip for distracting the vertebrae from the damaged vertebra, said means for fixing said clamps to said vertebra comprising first and second screws, wherein each of said clamps is provided with first and second openings adapted for receiving said first and second screws respectively therethrough, said openings being adapted to enable said screws to be oriented in the vertebra in a desired direction,
   b) a rigid elongate plate for interconnecting said pair of clamps having an opening provided at each opposite end and having a predetermined length between said openings which corresponds to the distance between said pair of clamps after distraction of the vertebrae from the damaged vertebra, and
   c) means for rigidly connecting together said rigid elongate plate and said pair of clamps.

12. A vertebral implant for the anterior removal and reconstruction of damaged vertebrae which comprises in combination:
   a) a pair of clamps, each provided with a means for fixing said clamp to a vertebra situated on either side of a damaged vertebra and provided with a means for supporting a forcep blade tip for distracting the vertebrae adjacent to the damaged vertebra, wherein each of said clamps has an anterior face for contacting against the associated vertebra which is provided with a convexity extending in a vertical direction along said face which complements the concavity of the vertebrae and a concavity extending in a horizontal direction along said face so that said clamps fit tightly against the anteroposterior convex lateral face of the vertebrae,
   b) a rigid elongate plate for interconnecting said pair of clamps having an opening provided at each opposite end and having a predetermined length between said openings which corresponds to the distance between said pair of clamps after distraction of the vertebrae from the damaged vertebra, and
   c) means for rigidly connecting together said rigid elongate plate and said pair of clamps.

* * * * *